(12) United States Patent
Busch et al.

(10) Patent No.: US 7,651,522 B2
(45) Date of Patent: Jan. 26, 2010

(54) MR-COMPATIBLE VASCULAR ENDOPROSTHESIS

(75) Inventors: Martin Busch, Witten (DE); Dietrich H. W. Grönemeyer, Alte Mühlenstrasse 45, D-45549 Sprockhövel (DE)

(73) Assignee: Dietrich H. W. Grönemeyer, Sprockhövel (DE)

( * ) Notice: Subject to any disclaimer, the term of this patent is extended or adjusted under 35 U.S.C. 154(b) by 89 days.

(21) Appl. No.: 11/541,832

(22) Filed: Oct. 2, 2006

(65) Prior Publication Data

US 2007/0106362 A1 May 10, 2007

(30) Foreign Application Priority Data

Oct. 1, 2005 (DE) .................. 10 2005 047 235

(51) Int. Cl.
*A61F 2/06* (2006.01)
(52) U.S. Cl. ................. 623/1.15; 623/1.54; 623/1.5
(58) Field of Classification Search ......... 623/1.4–1.54, 623/1.15; 128/6
See application file for complete search history.

(56) References Cited

U.S. PATENT DOCUMENTS

| 5,876,445 | A  | * | 3/1999  | Andersen et al. ........... 623/23.7 |
| 6,280,385 | B1 | * | 8/2001  | Melzer et al. ............... 600/423 |
| 2007/0168016 | A1 | * | 7/2007  | Gronemeyer et al. ...... 623/1.16 |
| 2007/0207186 | A1 | * | 9/2007  | Scanlon et al. .............. 424/424 |
| 2007/0244569 | A1 | * | 10/2007 | Weber et al. ............. 623/23.75 |
| 2008/0091259 | A1 | * | 4/2008  | Heggestuen et al. ....... 623/1.16 |

FOREIGN PATENT DOCUMENTS

EP      0 292 587 B1     11/1990

* cited by examiner

*Primary Examiner*—Suzette J Gherbi
(74) *Attorney, Agent, or Firm*—Collard & Roe, P.C.

(57) ABSTRACT

The invention relates to a medicinal implant or instrument, more particularly to a vascular endoprosthesis (1), having a radially dilatable hose part (2) comprised of a tubular knitted fabric of interdigitating meshes composed of one or more individual fibres (9). To provide such an implant or instrument that allows for MR-imaging of the interior of the implant or instrument, the invention proposes that the fibres (9) of the knitted fabric be electrically conductive and form an inductor (7, 8) within a high-frequency resonant circuit.

10 Claims, 2 Drawing Sheets

MR-COMPATIBLE VASCULAR ENDOPROSTHESIS

The invention relates to a medicinal implant or instrument, more particularly to a vascular endoprosthesis having a radially dilatable hose part comprised of a tubular knitted fabric of interlaced meshes composed of one or more individual fibres.

Vascular endoprostheses, so-called stents and other medicinal implants or instruments having a radially dilatable hose part like for example intravascular filter systems or vascular valves are known from prior art. For stents, the radially dilatable hose part is usually formed by lattice-like arranged metal filaments which are utilized to support and/or smoothen an injured coronary vessel wall. Similarly to a PTCA treatment, a stent is radially dilated by means of a balloon catheter in the area of the damaged location of the vessel to be treated and thereby fixed. Stents are mainly utilized to prevent acute vascular occlusion or restenosing after PTCA treatments. So-called stent grafts are taken to treat aneurysms.

The European patent no. EP 0 292 587 B1 discloses a vascular endoprosthesis having a radially dilatable flexible hose part, wherein the hose part is comprised of a tubular knitted fabric composed of interlaced meshes of one or more individual fibres. A benefit of this prior art vascular endoprosthesis is its high degree of flexibility in a non-dilated status and also in a dilated status. The tubular knitted fabric bears the advantage that the hose part made-up of it can be infinitely dilated radially within certain limits and thus be adapted unproblematically to the individual circumstances and conditions of a patient to be treated in a given case. Prior to its intended use, the endoprosthesis may be strongly reduced in its diameter, because the individual meshes of the knitted fabric interdigitate with a certain play. On extending the knitted fabric, the fibre sections within the interdigitating meshes of the knitted fabric experience a plastic deformation which causes the endoprosthesis to persist in its dilated position without requiring any further measures to fix it. Vascular endoprostheses having a radially dilatable hose part comprised of a knitted fabric thus offer the benefits of high flexibility accompanied with good inertia in the dilated position.

The diagnostic imaging of areas in the vicinity of a vascular endoprosthesis or a similar medicinal implant by means of magnetic resonance (MR) frequently turns out to be quite problematic. One reason might be that the implant existing in the body of an examined patient consists of a paramagnetic material. Owing to the magnetic susceptibility of the implant, the magnetic field in the otherwise diamagnetic surroundings of the implant is distorted, thereby causing artifacts in the scanned images. These images afflicted with artifacts in most cases are not usable for diagnostic purposes. Medicinal implants and instruments which are comprised of a hose part composed of a metallic lattice-like structure as is frequently the case with stents moreover have a disadvantage in that the lattice-like or net-like structure takes the effect of a Faraday's cage on MR-imaging so that the high-frequency fields irradiated during MR-imaging do not penetrate into the volume within the implant. Owing to this screening, the interior of a conventional stent disadvantageously remains invisible in MR-imaging. More particularly it is a drawback because it is thereby prevented that a restenosing in the interior of a stent can be diagnosed by means of MR-imaging at a fairly early stage.

Now, therefore, it is the object of the present invention to advance the development of a medicinal implant or instrument, more particularly a vascular endoprosthesis, to such a level that MR-imaging, more particularly of the interior of the implant, is possible.

The present invention achieves this object on the basis of a medicinal implant or instrument of the type described hereinabove in such a way that the fibres of the knitted fabric are electrically conductive and form an inductor within a high-frequency resonance circuit.

Hence, in accordance with the present invention, the radially dilatable hose part is made of electrically conductive fibres which create inductivity within a high-frequency (or radio-frequency, RF) resonant circuit. The desired MR-compatibility is achieved thereby. The knitted fabric of the dilatable hose part as defined by this invention has an electric impedance. In this way, a resonator structure is thus created that can be utilized in MR-imaging. To this effect the resonance frequency of the high-frequency resonant circuit must have been adapted to the resonance frequency of the applied MR-device. Then, the high-frequency fields irradiated on MR-imaging are not screened as it is the case with conventional stents but—on the contrary—even intensified in the interior of the implant. Thereby an MR-imaging of the volume within the hose part of the implant embodying this invention is particularly well possible.

With the medicinal implant or instrument embodying this invention, the fibres of the knitted fabric are expediently isolated electrically against each other in the crossover points of the meshes. The fibres may advantageously be metal wires having an electrically isolating coating. The isolation in the crossover points is necessary to be able to adjust the inductivity of the resonator structure as required. Without an isolation, short-circuits would occur in the area of the crossover points. In accordance with a viable configuration of the present invention, the fibres may be connected with each other electroconductively at least in some of the crossover points of the meshes. At some crossover points, electrical connections can be created in a well-aimed manner in order to adjust inductivity to the desired level so that the resonator structure is harmonized and well-adapted to the resonance frequency of the applied MR-device. A well-aimed electroconductive connection in at least some of the crossover points can be utilized to define current paths within the knitted fabric of the hose part. The course of these current paths will then determine impedance.

In conformity with a purposeful embodiment of the medicinal implant or instrument embodying this invention, the knitted fabric is so manufactured that the fibres form no closed-circuit current paths within the knitted fabric. It is thereby prevented that eddy currents develop on the surface of the hose part during MR-imaging due to high-frequency fields irradiated from outside. Thus the medicinal implant embodying this invention does not screen the irradiated high-frequency fields. The hose part cannot take the effect of a Faraday's cage.

In accordance with an advantageous configuration of the medicinal implant or instrument embodying this invention, the knitted fabric of the hose part may be so manufactured that the fibres along the longitudinal extension of the hose part at least form a helix-shaped current path or current path section. For example, it is possible to manufacture the entire hose part by knitting from a straight electrically isolated metal wire. After all, a helix-shaped wire structure having the properties of a solenoid coil and being particularly apt to create inductivity is formed in this way. The prerequisite to be fulfilled is that the fibre sections in the crossover points of the meshes are electrically isolated against each other. As described before, electrically conductive connections can be selectively established at individual crossover points of the meshes, for example in order to specify the number of effective windings of the solenoid coil and thereby adjusting inductivity. It is also conceivable to provide a saddle coil by way of a well-aimed electroconductive connection of the fibre sections.

If the hose part of the medicinal implant or instrument embodying this invention is configured in the way of a solenoid or saddle coil, the polarization level of the high-frequency field generated in the interior of the hose part during MR-imaging is parallel to the longitudinal extension of the hose part. With a vascular endoprosthesis, depending on the position of the prosthesis in the body of a patient, it may be required for imaging of the interior of the prosthesis that the high-frequency field is polarized in one plane vertically to the longitudinal extension of the hose part. In this case, the knitted fabric of the hose part is effectively so manufactured that the fibres form at least a current path or current path section running in parallel to the longitudinal extension of the hose part. It is of special advantage to arrange two or more current paths or current path sections running in parallel to the longitudinal extension of the hose part in an arrangement that is well spread over the circumference of the hose part. In case of this configuration, a resonator structure is generated that is similar to a birdcage coil. With such a resonator structure, the current paths running in parallel to the longitudinal extension of the resonator are connected to each other at the front side of the resonator through capacitors. Likewise, capacitors may be interconnected into the current paths spread over the circumference of the resonator.

In conformity with a particularly advantageous embodiment, the hose part of the medicinal implant or instrument embodying this invention is comprised of at least two knitting layers wrapped around each other. The knitting layers wrapped around each other may indeed be of a different configuration. Accordingly, a particularly high flexibility is given with regard to the adjustment of the inductivity of the resonator structure. Moreover, a multiple-layer configuration of the hose part has the benefit of providing increased resistivity versus force impacts from the exterior.

The hose part of the medicinal implant or instrument embodying this invention can be manufactured from individual fibres by knitting, crocheting, knotting, or other mesh-forming techniques. Eligible are the most different well-known knitting, crocheting, weaving and knotting patterns. The pattern is chosen depending on the desired properties of the resonator structure to be generated.

Furthermore it is of advantage if the knitted fabric of the hose part with the medicinal implant or instrument embodying this invention has a loose end so that the knitted fabric can be dissolved by pulling at the loose end. Dissolving a knitted fabric by pulling at a loose end is also described as "rubbing-up". Nowadays, a technique often applied is removing vascular endoprostheses from a treated blood vessel after a certain period of time. With the implant embodying this invention, this can be done in a very simple manner by rubbing-up the knitted fabric.

Examples for embodiments of this invention are described in greater detail in the following, taking reference to the accompanying drawings, in which.

Figure 1:
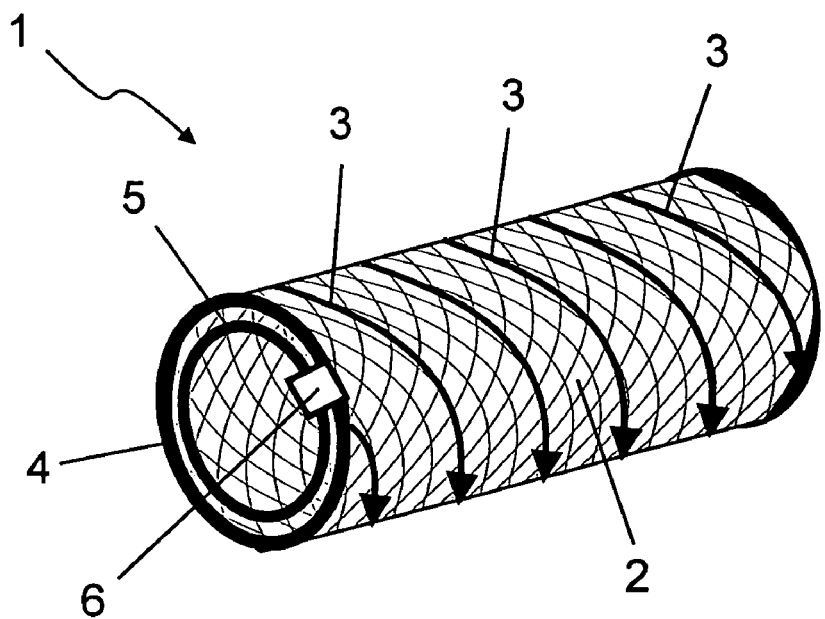
FIG. 1 shows a three-dimensional schematic view of a vascular endoprosthesis embodying this invention.

The implant described in FIG. 1 is a stent which is entirely designated with reference number 1. The stent 1 is comprised of a radially dilatable hose part 2 comprised of a tubular knitted fabric with interdigitating meshes composed of one or more individual fibres. The structure of the knitted fabric is explained in greater detail further below by taking reference to FIGS. 3 and 4. The fibres of the knitted fabric are electrically conductive and form an inductor within a high-frequency resonant circuit. The knitted fabric is so manufactured that the fibres along the longitudinal extension of hose part 2 form a helix-shaped current path 3 which continuously extends from one end of the hose part 2 to the other end. In the example of an embodiment illustrated in FIG. 1, the hose part 2 is composed of two knitted fabric layers, i.e. from an exterior knitted fabric layer 4 and an interior knitted fabric layer 5. The knitted fabric of the inner knitted fabric layer 5, too, is so configured that a helix-shaped current path is formed which extends from one end of the hose part 2 to the opposite end. The sense of rotation of the helix of the interior knitted fabric layer 5 is opposite to the sense of rotation of the helix of the exterior knitted fabric layer 4. The current paths formed by the fibres of the two knitted fabric layers 4 and 5 are connected with each other through capacitors 6 at the ends of the hose part 2. In FIG. 1 only the capacitor at the front end of the hose part 2 can be identified. The capacitors 6 need not necessarily be configured as separate switching elements. The capacitors 6 may also be formed by the overlying electrically conductive areas of the knitted fabric layers 4 and 5.

Figure 2:
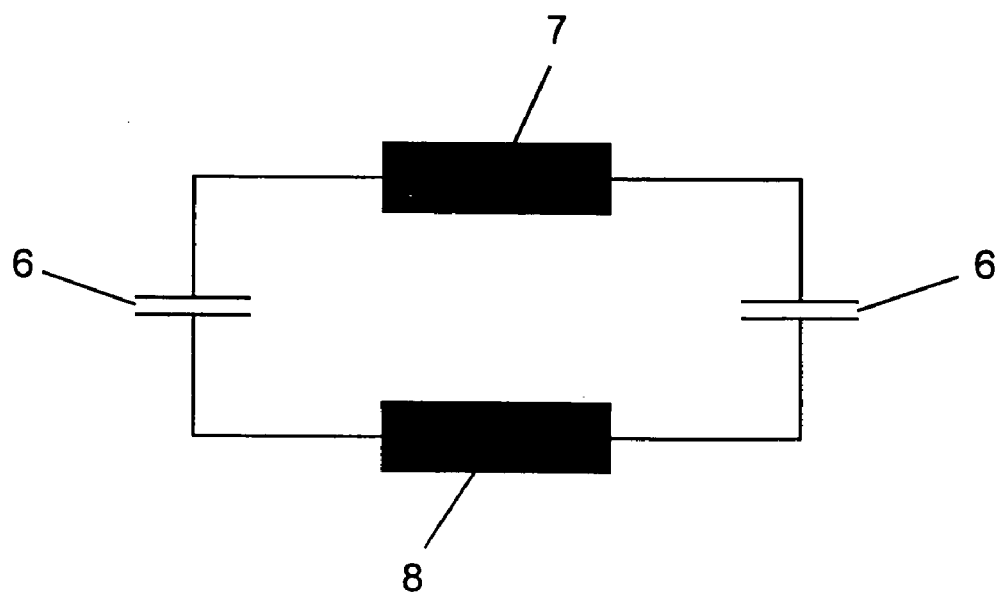
FIG. 2 shows a substitute circuit diagram to elucidate the resonator properties of the implant embodying this invention.

Based upon the circuit diagram as per FIG. 2 it becomes evident how the inductors 7 and 8 formed by the knitted fabric layers 4 and 5 are interconnected via capacitors 6. The inductor 7 is allocated to the exterior knitted fabric layer 4 of stent 1, while the inductor 8 is allocated to the inner knitted fabric layer 5. On the whole, a resonator is thus created, i.e. a high-frequency resonant circuit, wherein the inductors 7 and 8 as well as the capacitors 6 are so harmonized to each other that the resonance frequency is adapted to that of a MR device.

Figure 3:
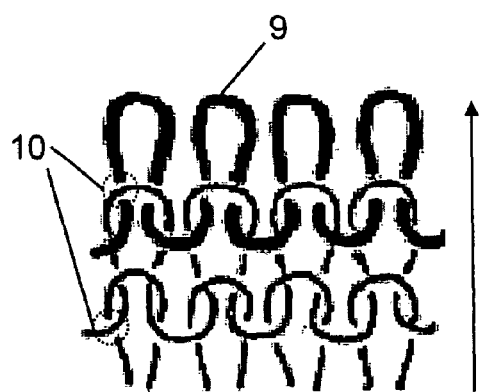
FIG. 3 shows an enlarged detail of the knitted fabric of the implant embodying this invention in accordance with a first variant.
Figure 4:
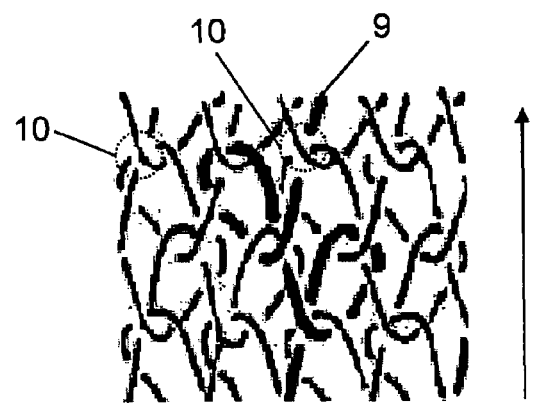
FIG. 4 shows a detail of the knitted fabric in accordance with a second variant.

FIGS. 3 and 4 are planar representations of a detail from the knitted fabric of the radially dilatable hose part 2 of the vascular endoprosthesis 1 embodying this invention. FIG. 3 shows a pattern of interdigitating meshes that can be manufactured from a single electrically conductive wire 9, for example by knitting around a cylindrical core. In crossover points 10 of the meshes, the sections of the wire 9 are electrically isolated against each other. Taking the pattern illustrated in FIG. 3, it is possible to form a cylindrical knitted fabric in which after all a straight helix-shaped current path extending from one end of the hose part 2 to the opposite end is formed along the longitudinal extension of said hose part 2. FIG. 4 shows another viable pattern of a knitted fabric in which the individual meshes interdigitate like a chain. The course of the individual fibres within the knitted fabric may be gathered quite well from FIG. 4 based upon the individual fibre 9 illustrated in bold style. The pattern shown in FIG. 4 is well apt for manufacturing a knitted fabric in which the fibres 9 of the knitted fabric form several current paths or current path sections running in parallel to the longitudinal extension of said hose part 2. Indicatively shown by arrows in FIG. 3 and 4 is the direction of the longitudinal extension of said hose part 2. With the pattern shown in FIG. 4, too, the fibres 9 in the crossover points 10 of the meshes are electrically isolated against each other. The patterns illustrated in FIGS. 3 and 4 are particularly easy to manufacture from metal wires 9 which have an electrically isolating coating.

Figure 5:
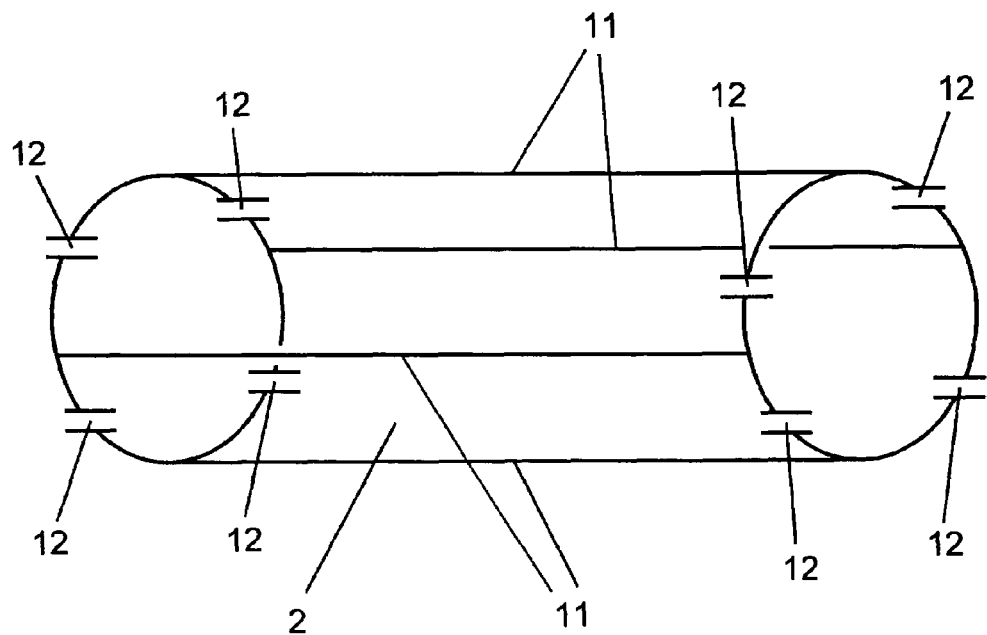
FIG. 5 shows a schematic view of the resonator structure embodying this invention.

FIG. 5 schematically shows a resonator structure which can be set-up according to this invention, for example, by a hose part 2 from a knitted fabric of the type shown in FIG. 4. Accordingly, several current paths are evenly spread over the circumference of said hose part 2. At the opposite ends of said hose part 2 the current paths 11 formed by the fibres 9 of the knitted fabric are connected with each other via capacitors 12. After all, a birdcage resonator is established whose resonance frequency is harmonized via an appropriate harmonization of the capacitors 12 to the resonance frequency of the applied MR device. The birdcage resonator offers the benefit that the polarization level of the high-frequency field generated within the resonator runs vertically to the longitudinal extension of said hose part 2. A resonance structure of this type makes it possible to examine the interior of said stent 1 by means of MR imaging, if the stent is located in a blood vessel that mainly runs in parallel to the body length axis of a patient. With frequently applied closed-type MR devices, the external static magnetic field also runs in parallel to the body length axis. For imaging, it is important that the high-frequency field is polarized in one plane vertically to the direction of the static magnetic field.

What is claimed is:

1. An MR-compatible medicinal implant or instrument, comprising a radially dilatable hose part composed of a tubular knitted fabric of interdigitating meshes having crossover points, said fabric comprising at least one individual fiber, the individual fibre being a metal wire, wherein the individual fiber comprises an electrically isolating coating and wherein some of the crossover points of the meshes are electroconductive.

2. The medicinal implant or instrument as defined in claim 1, wherein the at least one individual fiber comprises a plurality of fibers comprises a plurality of fibers (9) electrically isolated against each other in the crossover points of the meshes.

3. The medicinal implant or instrument as defined in claim 1, wherein the knitted fabric is so manufactured that the at least one individual fiber forms no closed-circuit current paths within said knitted fabric.

4. The medicinal implant or instrument as defined in claim 1, wherein the knitted fabric is so manufactured that the at least one individual fiber forms at least one helix-shaped current path or current path section along a longitudinal extension of said hose part.

5. The medicinal implant or instrument as defined in claim 1, wherein the knitted fabric is so manufactured that the at least one individual fiber forms at least one current path or current path section running in parallel to a longitudinal extension of said hose part.

6. The medicinal implant or instrument as defined in claim 5, wherein two or more current paths or current path sections running in parallel to the longitudinal extension of said hose part are spread circumferentially over said hose part (2).

7. The medicinal implant or instrument as defined in claim 1, wherein the knitted fabric is so manufactured so that the at least one individual fiber forms current paths or current path sections connected to each other via at least one electrical capacitor.

8. The medicinal implant or instrument as defined in claim 1, wherein the hose part comprises at least two knitted fabric layers wrapped around each other.

9. The medicinal implant or instrument as defined in claim 1, wherein the hose part can be manufactured from the at least one individual fiber by knitting, crocheting, weaving, knotting or other mesh-forming techniques.

10. The medicinal implant or instrument as defined in claim 1, wherein the knitted fabric of said hose part has a loose end so that the knitted fabric can be dissolved by pulling at the loose end.

* * * * *